(12) United States Patent
Basañez et al.

(10) Patent No.: US 9,642,744 B2
(45) Date of Patent: May 9, 2017

(54) CONTACT LENS HANDLING DEVICE

(71) Applicants: Xabier Basañez, San Antonio, TX (US); Alejandra Hernández Molina, San Antonio, TX (US); Analaura Villarreal Berain, San Antonio, TX (US); David Zhang, San Antonio, TX (US)

(72) Inventors: Xabier Basañez, San Antonio, TX (US); Alejandra Hernández Molina, San Antonio, TX (US); Analaura Villarreal Berain, San Antonio, TX (US); David Zhang, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/141,471

(22) Filed: Apr. 28, 2016

(65) Prior Publication Data
US 2017/0071786 A1 Mar. 16, 2017

Related U.S. Application Data

(60) Provisional application No. 62/154,005, filed on Apr. 28, 2015.

(51) Int. Cl.
A61F 9/00 (2006.01)
B08B 11/02 (2006.01)
B08B 7/00 (2006.01)
B08B 3/04 (2006.01)
A45C 11/00 (2006.01)

(52) U.S. Cl.
CPC .......... *A61F 9/0061* (2013.01); *A45C 11/005* (2013.01); *B08B 3/04* (2013.01); *B08B 7/0057* (2013.01); *B08B 11/02* (2013.01)

(58) Field of Classification Search
CPC ..... A61F 9/0061; A45C 11/04; A45C 11/005; B08B 3/04; B08B 7/0057; B08B 11/02; A61L 2/08; A61L 2/10
See application file for complete search history.

(56) References Cited

U.S. PATENT DOCUMENTS

| | | | | |
|---|---|---|---|---|
| 3,910,618 A | * | 10/1975 | Massenz | A61F 9/0061 294/1.2 |
| 5,144,144 A | * | 9/1992 | Borovsky | A61L 12/063 250/455.11 |
| 5,348,358 A | * | 9/1994 | Selick | A61F 9/0061 294/1.2 |
| 6,193,806 B1 | * | 2/2001 | Reed | A45C 11/005 134/1 |

(Continued)

*Primary Examiner* — David E Smith
(74) *Attorney, Agent, or Firm* — Norton Rose Fulbright US LLP

(57) ABSTRACT

Certain embodiments are directed to a contact lens application/removal device comprising a plurality of removably interconnection components. The components include a lens handling tip, a lubrication fluid container, two detachable storage chambers, and, optionally, a detachable ultraviolet disinfection system. The device can be used for contact lens removal, lubrication, storage, and application to the eye without the need for direct contact with the fingers or skin of a subject applying and the lenses.

12 Claims, 17 Drawing Sheets

(56) References Cited

U.S. PATENT DOCUMENTS

2007/0206377 A1\* 9/2007 Borup ................ A45C 11/005
  362/156
2011/0024649 A1\* 2/2011 Merkle ............... A45C 11/005
  250/492.1

\* cited by examiner

CONTACT LENS HANDLING DEVICE

BACKGROUND

According to the FDA, an estimated 30 million people use contact lenses in the U.S. alone (Federal Drug Administration (2010). *Looking Good: Safe Use and Care of Contact Lenses* [Online at fda.gov/forhealthprofessionals/articlesofinterest/ucm211838.htm]). The major reasons why glass wearers do not use contact lenses is the discomfort of directly touching the eye with their fingers, the fear of infecting or damaging their eye, and the inability to remove or lubricate the lenses when they do not have access to disinfection equipment. If unhygienic methods or processes were used, then ocular diseases can develop, such as dry eye, eye infections, etc. For these reasons, there exists a need for a hygienic method to apply, remove, and lubricate contact lenses without a direct finger and eye contact.

SUMMARY

Certain embodiments are directed to a contact lens application/removal device comprising a plurality of removably interconnection components. The components include a lens handling tip, a lubrication fluid container, two detachable lens storage chambers, and, optionally, a detachable ultraviolet disinfection system. The device can be used for contact lens removal, lubrication, storage, and application to the eye without the need for direct contact with the fingers or skin of a subject applying the lenses. The detachable ultraviolet disinfection system disinfects the lens-handling tip before, after, or before and after each use. The lens-handling device uses the physical principle of surface tension to its advantage for the removal and application of contact lens from and into the wearer's eye.

The characteristics and design herein discussed are subject to variations with regards to specific components, arrangement of these components, use of these components, shape of these components.

Certain embodiments are directed to a contact lens storage and application device comprising: a body comprising a plurality of interlocking segments, the interlocking segments including (i) a disinfection segment, (ii) an application/reservoir segment, (iii) a first lens storage container, and (iv) a second lens storage container, and, wherein each segment is removably connected to an adjacent segment; the disinfecting segment comprises a compartment housing a UV light source with the bottom portion configured to connect with a segment adjacent to the bottom portion and a top configured to connect with a segment adjacent to the top portion; the handler (handling mechanism)/reservoir segment comprises an outer wall forming a container having an open end configured to receive the disinfection segment and a closed end having an end wall configured to connect with an adjacent segment, within the container is a fluid reservoir having a fluid port extending to the exterior of the container to provide for movement of fluids in and out of the reservoir, a handling mechanism traverses the reservoir and is connected to the end wall and extends beyond reservoir terminating in a lens delivery portion having a concave lens-handling tip that complements and secures a lens, the handling portion has a central moveable rod that pass through the container end wall and terminates in a platform, having a spring spacer between the platform and end wall, the handling mechanism is configured such that pushing the platform extends the central rod providing for the release of a lens during application and retraction of the rod provides for securing a lens during removal; the first lens storage segment comprises a first lens storage container having a convex lens support positioned in the bottom of the container with the base of the container configured to connect with a segment adjacent to the bottom portion and a top configured to connect with a segment adjacent to the top portion of the storage container; the second lens storage segment comprises a second lens storage container having a convex lens support positioned in the bottom of the container with the base of the container configured to connect with a segment adjacent to the bottom portion and a top configured to connect with a segment adjacent to the top portion of the storage container.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
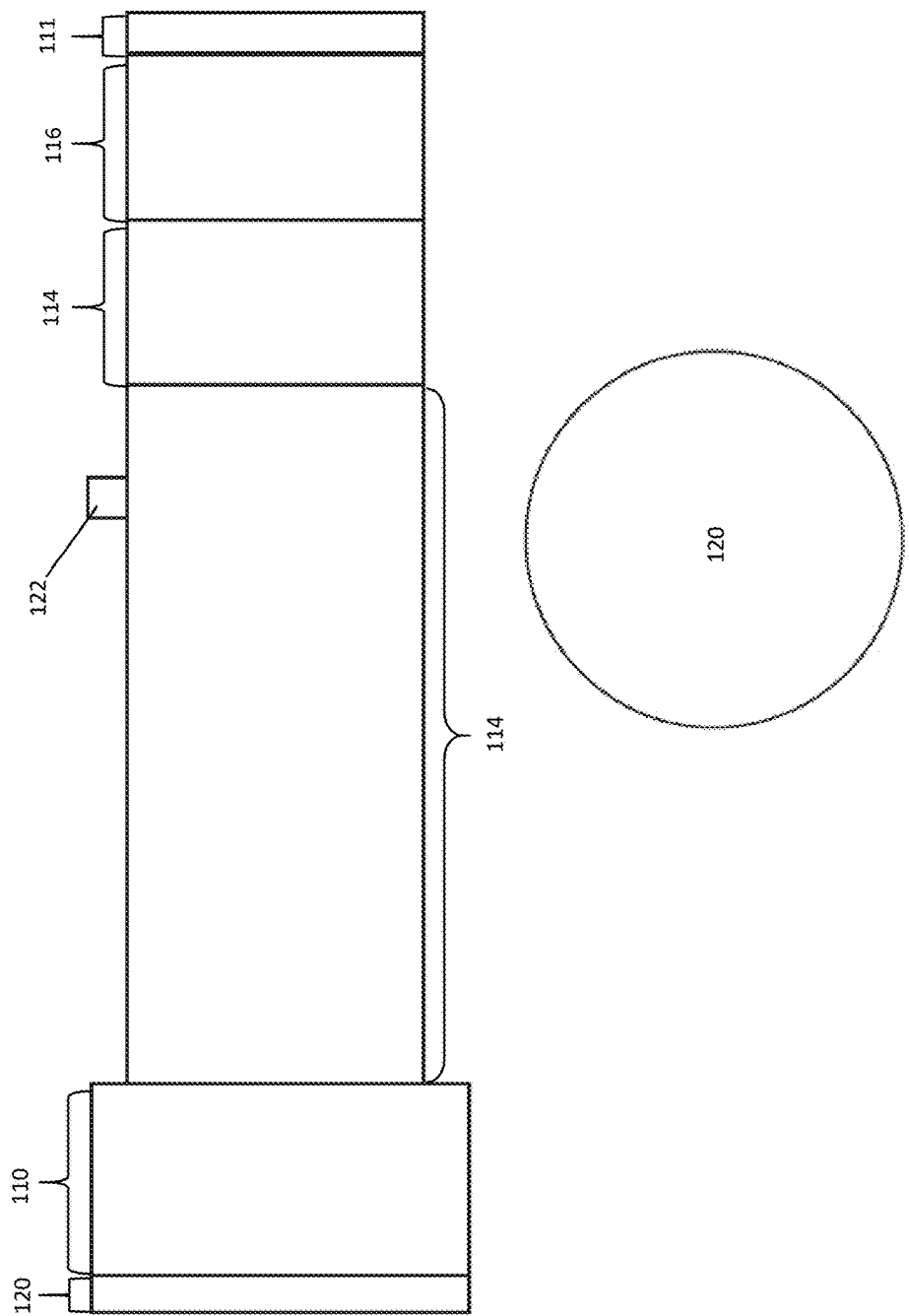
FIG. 1. Illustration of one embodiment of the device assembled.

Certain embodiments are directed to a device comprising a plurality of detachable segments. Referring to FIG. 1, the segments can include a first cap 120, handling mechanism/fluid reservoir segment 112, lens storage segments 114 and 116, ultraviolet disinfection segment 110, and second cap 111. Each of the segments is configured to be reversibly connected to adjacent segments. The segments can be provided in any order. In certain aspects the segments are connected by a screw mechanism or other locking mechanism that allows adjacent segments to be interlocked in a stacked fashion. In certain aspect the interlocking mechanism forms a water seal between adjacent segments. The segments may be assembled linearly in any order due to their interchangeability resulting from the presence of complementary screwing patterns at their ends.

Handling Mechanism/Fluid Reservoir Segment.

Figure 2:
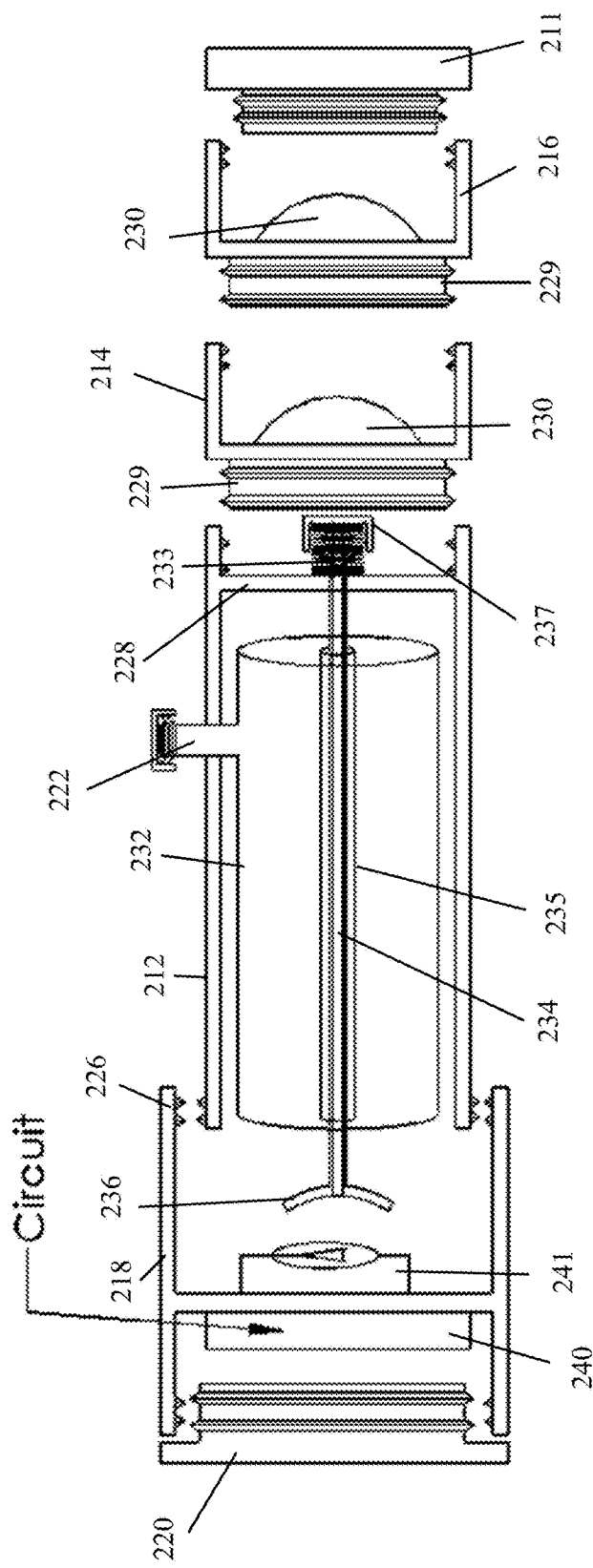
FIG. 2. Illustration of the embodiment of the device in FIG. 1 in cross section and in exploded view.

The handling mechanism/fluid reservoir segment comprises a compartment containing a handling mechanism, lubrication reservoir, and can be capped with a screw cap or another adjacent segment. As seen in FIG. 2, handling mechanism/fluid reservoir segment 212 comprises fluid reservoir 232 surrounding sheath 235. Sheath 235 forms a lumen through which inner movable rod 234 is positioned. Rod 234 is connected at one end with a circular, concave device-lens interface (lens-handing tip) 236 and on the other end forms platform 237 that is configured to be pressed and release, moving the rod along the long axis of the mechanism, while applying or removing, respectively, the lens from an eye. The concave surface has a pattern to optimize the contact length between lens and device so as to achieve a sufficient tension force to overcome the forces holding the lens to the wearer's eye. At the device-lens interface 236, a rubbery material is provided to protect the eye from scratching or puncture by the mechanism. In a further aspect the space between fluid reservoir 232 and sheath 235 is filled with a ring made of a rubbery material to prevent inflow and stagnation of liquid. At the opposite side of the device-lens interface 236 and on the outside of end wall 228 the inner rod 234 extends outwards and forms platform 237. Spring 233 surrounds rod 234 and is positioned between end wall 228 and platform 237 so that the inner rod 234 can be pushed in the direction of device-lens interface 236 during application of the lens to the user's eye and released during removal of a lens from a user's eye. When activated, the pushing mechanism move rod 234 into the cavity of the lens-handling tip resulting in a smaller force holding the lens to the device, so that surface tension forces between the user's eye and the lens can easily dominate, and thus the lens is placed effortlessly on the eye. When platform 237 is released, inner rod 234 retracts to its original position, therefore restoring the continuity of the surface at lens-device interface 236 and forming contact sufficient to remove the lens from the eye.

Reservoir 232 is positioned inside handling mechanism/fluid reservoir segment 212 and can be in the shape of a thick-walled cylinder, which surrounds sheath 235 of the handling mechanism. The reservoir need not have a circular cross section, but can have various cross section shapes, such as a square of other polygon. Opposite device-lens interface 236, fluid port 222 extends beyond reservoir 232 and traverses the handling mechanism/fluid reservoir wall. Fluid port 222 provides for refilling the reservoir or removing lubricant when needed. The end of the fluid port external to handling mechanism/reservoir segment 212 is closed with a sealing cap, which the user can screw in and out as needed. The handling mechanism and fluid reservoir allow the user to apply, remove, and lubricate the contact lenses without direct contact of fingers with the lenses in a simple manner.

Lens Storage Segments.

In certain aspects two storage compartments 214 and 216 are included in the device, one for each lens. Each of these segments form compartments that can be connected to adjacent segments. In certain aspect the top and bottom portions are configured with a screw mechanism that is compatible with an adjacent segment. Each of these compartments is designed to store the lens in solution (i.e. the compartment can be filled by pouring lubricant fluid into one of the parts, and then closing the compartment with by connecting with a adjacent segment). The bottom surface of the compartment convex surface protruding into the lumen of the compartment that is configured to support a contact lens and position the lens for interaction with the handling mechanism. The handling mechanism can be removed from the device and used to manipulate the lens for application or removal. An adjacent segment will have a concave portion that complements the convex lens support to hold the lens in place so that it remains on the lens support even if the device is moved. In the absence of a holding mechanism, the lens could move freely inside the compartment, making it difficult to retrieve with the handling mechanism when the user wishes to apply the lens to their eye. The complementarity of these compartments preserves the shape of the lens, preventing the lens from inverting (something that commonly happens with current commercially available lens cases) The lens storage segments allow the user to store contact lenses in a safe and efficient manner. The contact lenses are kept in solution for storage, which preserves the integrity of the lens since they are kept hydrated during the storage period.

Ultraviolet Disinfection Segment.

Disinfection segment 218 forms a compartment used to disinfect the handling mechanism tip after, before, or before and after each use, depending on the user's preference. It can be attached to the handling mechanism/fluid reservoir segment 212 where it is configured to illuminate lens-device interface 236. Disinfection segment 218 can comprise an integrated ultraviolet light emitting source 241 (possibly a UV lamp or UV LED) coupled to circuit 240 which, when turned on, is capable of disinfecting the handling tip 236 of the device. In certain aspects the UV source can be one or more light emitting diodes (a LED). The feasibility of this compartment is based on a commercially available and successful device for disinfecting the head of toothbrushes, which uses an UV lamp circuit. UV radiation with wavelength between 200-320 nm is known to be effective at eliminating airborne and surface microorganisms (e.g. bacteria, viruses, yeast, and molds). Moreover, bacterial DNA is known to have a peak UV absorbance at 254 nm with regards to germicidal effects, electromagnetic radiation at this specific wavelength is the most effective at destroying bacterial DNA. Disinfection compartment allows for the disinfection of key elements of the handling mechanism and will provide the user with higher level of hygiene. This disinfection mechanism will help in minimizing, if not eliminating, the occurrence of possible eye infections.

The device can have a length no larger than 16 cm (i.e. 6 inches) when all segments are assembled together, which ensures that the device may be stored and carried in a reduced space. The outer dimensions of each compartment can be such that they have complementary screw patterns for linear interlocking in any order desired. Similarly, the inner dimensions of the lens storage segments are such that commercially available contact lenses fit inside (i.e. the inner diameter of these compartments will be slightly larger than the maximum diameter of commercially available contact lenses, which is 14.5 mm). The handling mechanism tip 236 can have a smaller diameter than the contact lens since this will be more comfortable for the user when removing the lens from the eye. The inner rod for inserting the lens has a diameter in the range of 2 mm so that when pushing the lens onto the eye, the surface tension forces between lens and eye can easily dominate. The volume of lubricant fluid needed for several uses determines the volume of lubrication fluid reservoir, and thus its dimensions. The dimensions can be in accordance to the ASTM standards for portable devices.

Figure 3:
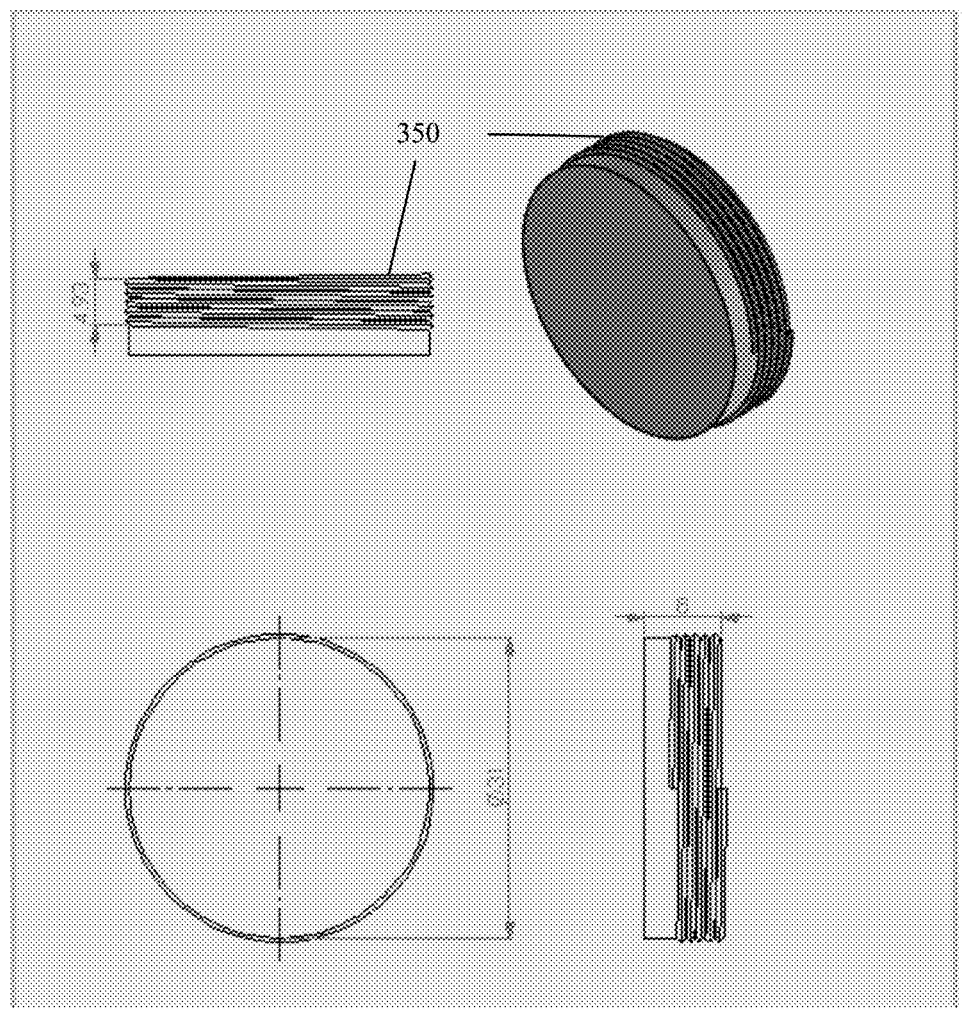
FIG. 3. Illustration of one embodiment of a disinfection case cap.
Figure 4:
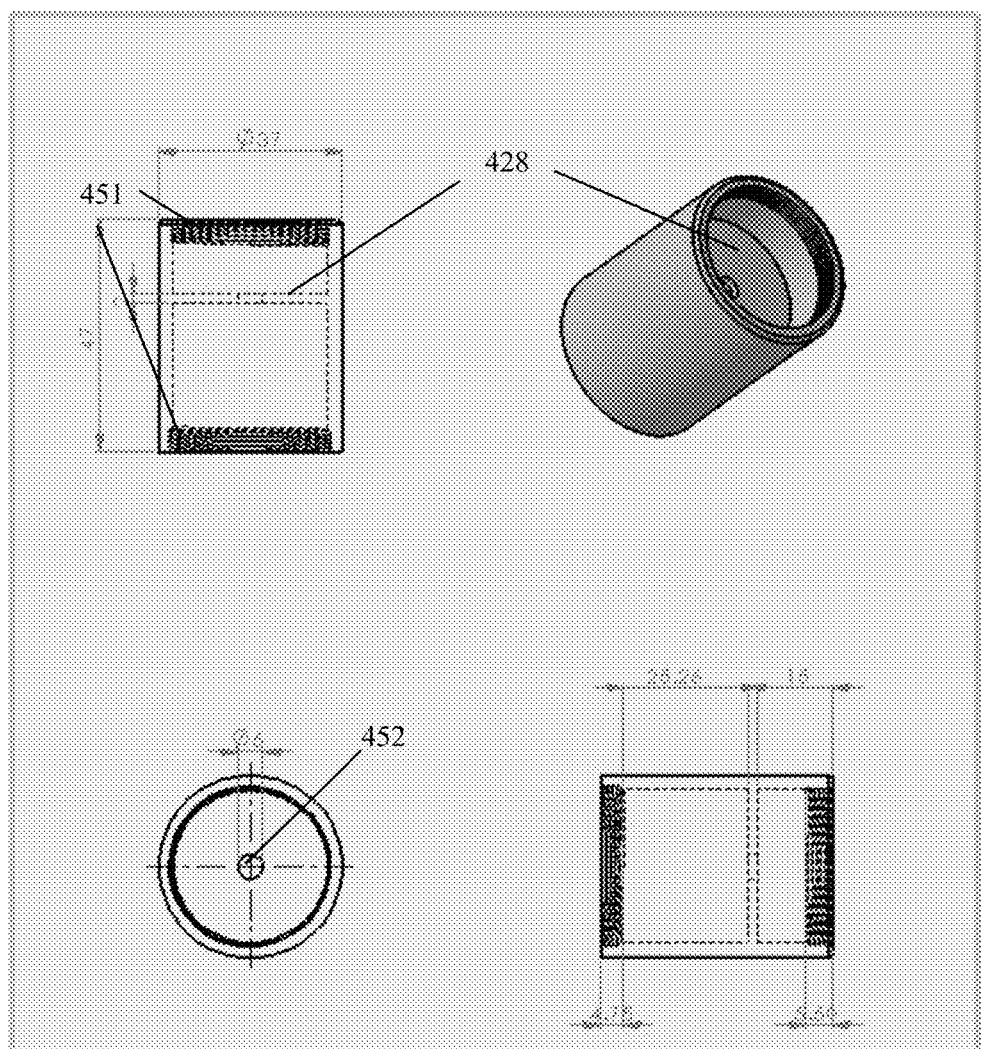
FIG. 4. Illustration of one embodiment of a handling mechanism cap.
Figure 5:
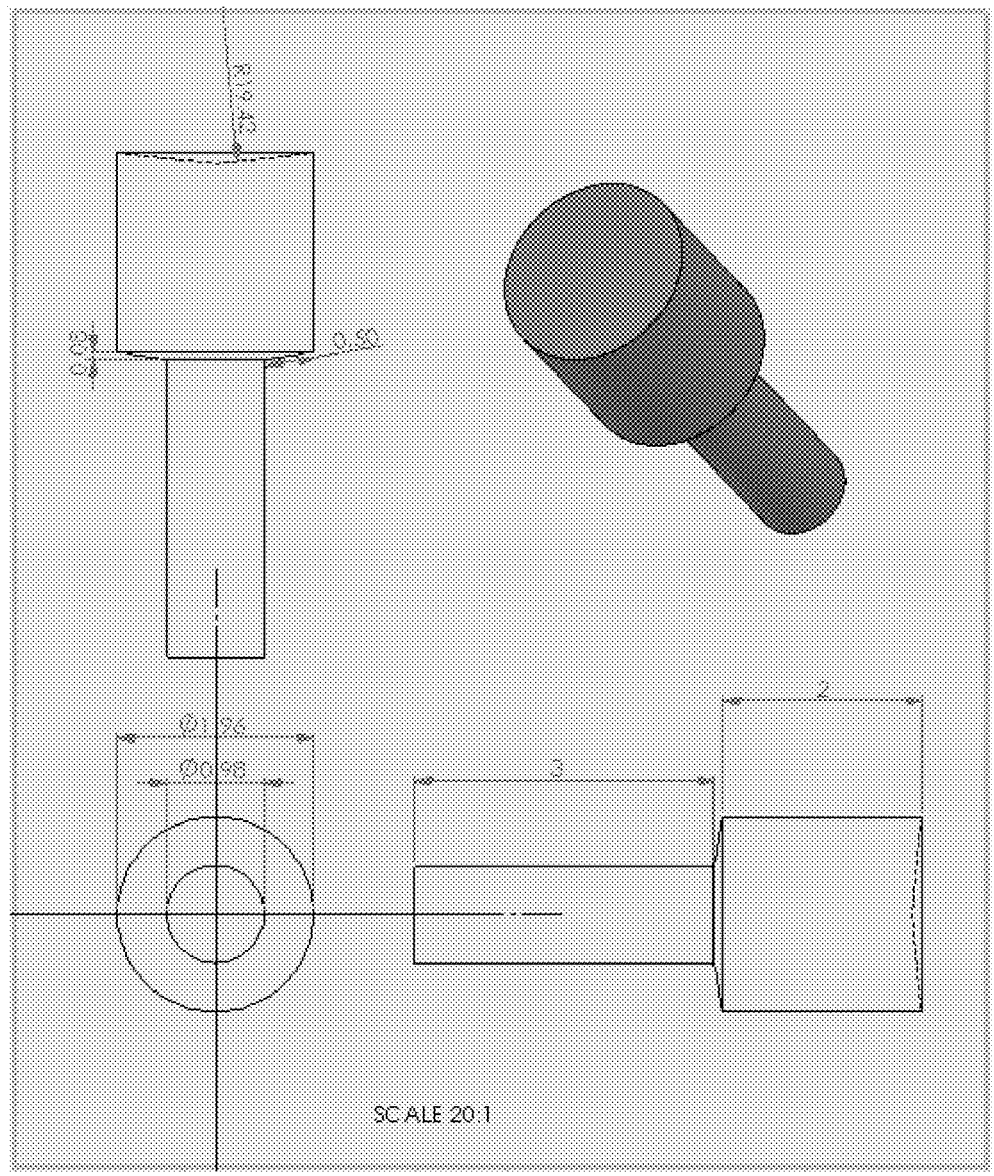
FIG. 5. Illustration of one embodiment of an inner sheath silicone cover.
Figure 6:
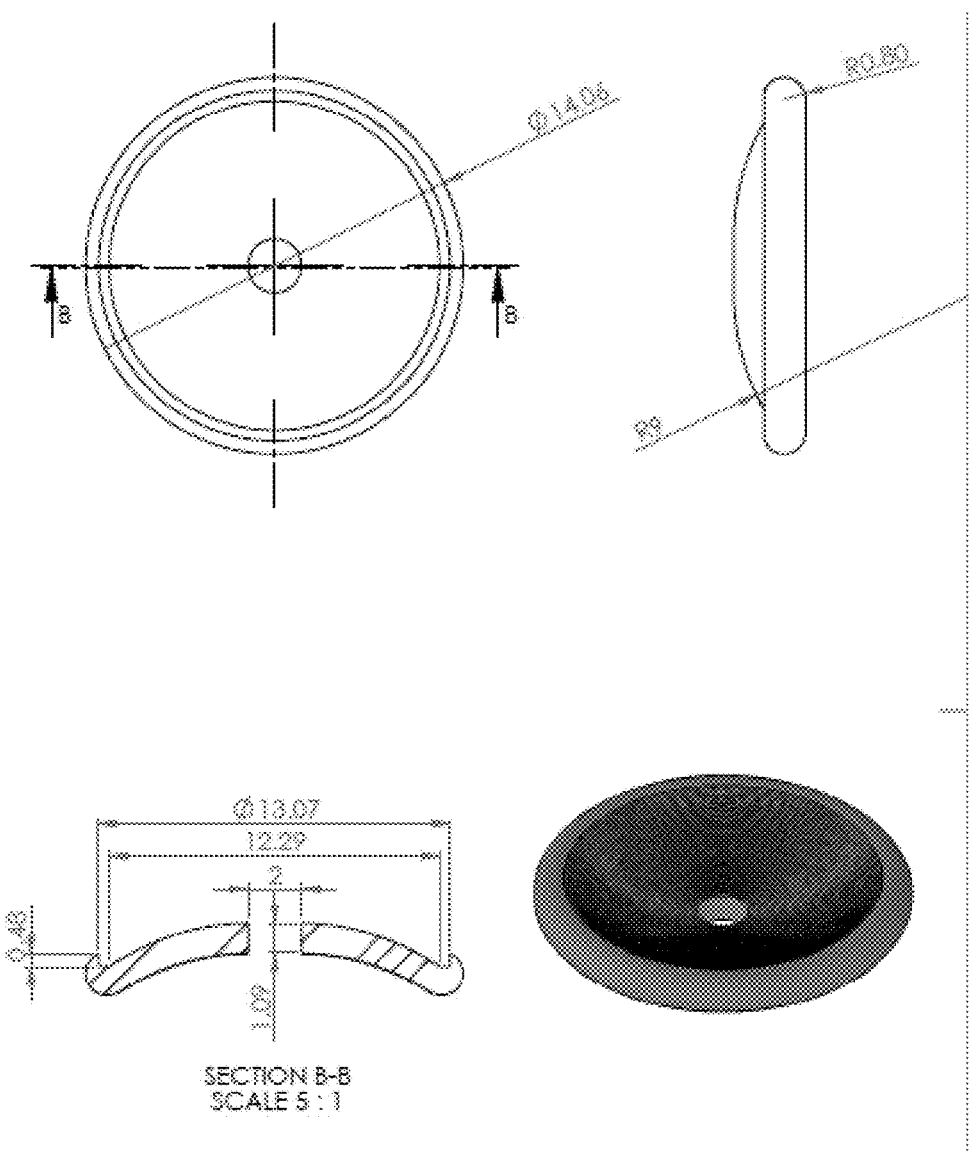
FIG. 6. Illustration of one embodiment of an outer sheath silicone cover.
Figure 7:
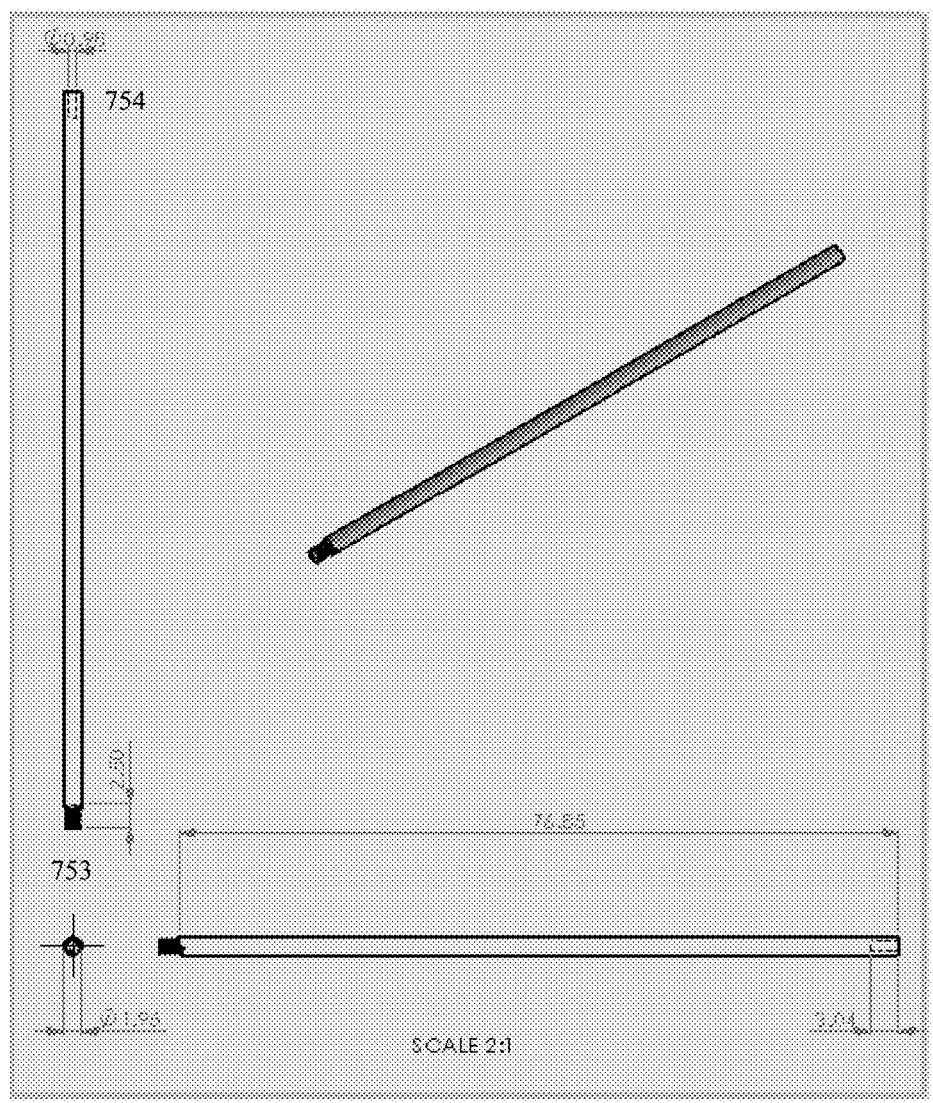
FIG. 7. Illustration of one embodiment of an inner sheath component.
Figure 8:
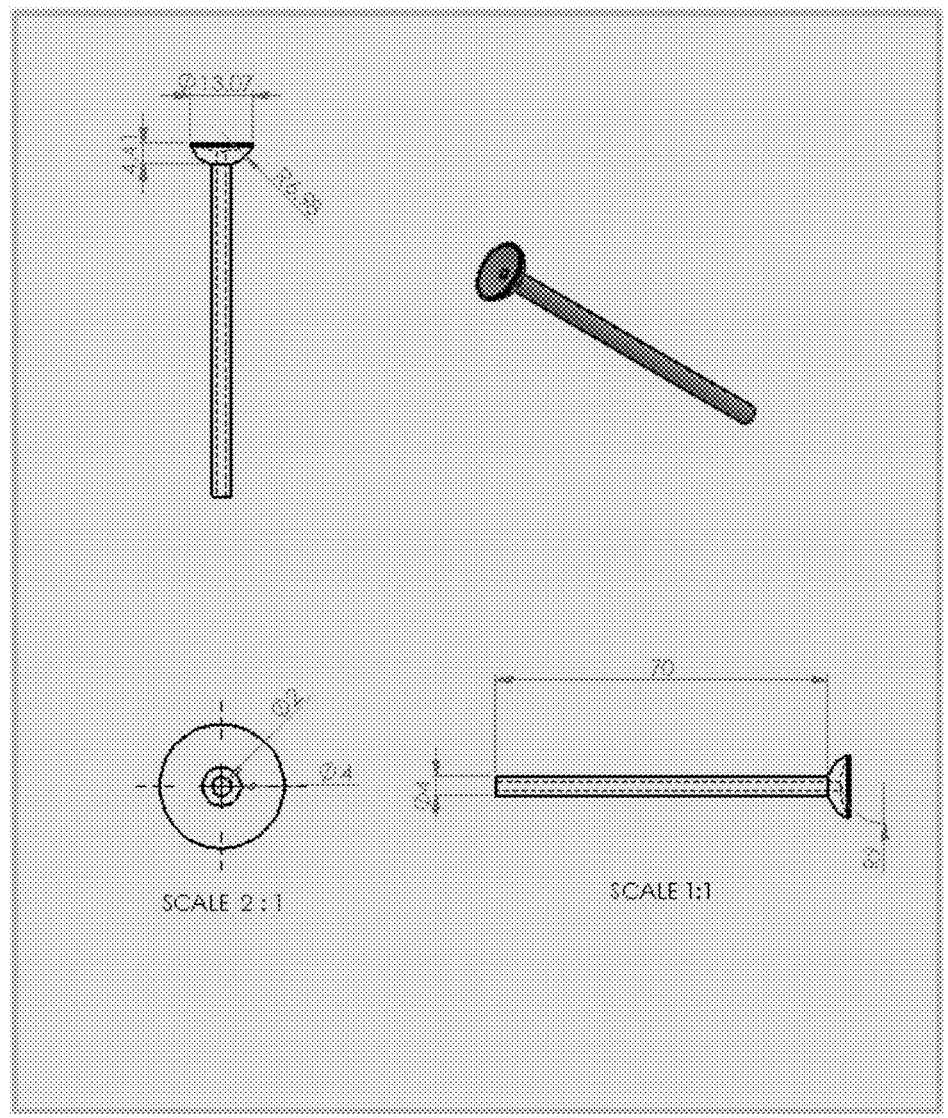
FIG. 8. Illustration of one embodiment of an outer sheath component.
Figure 9:
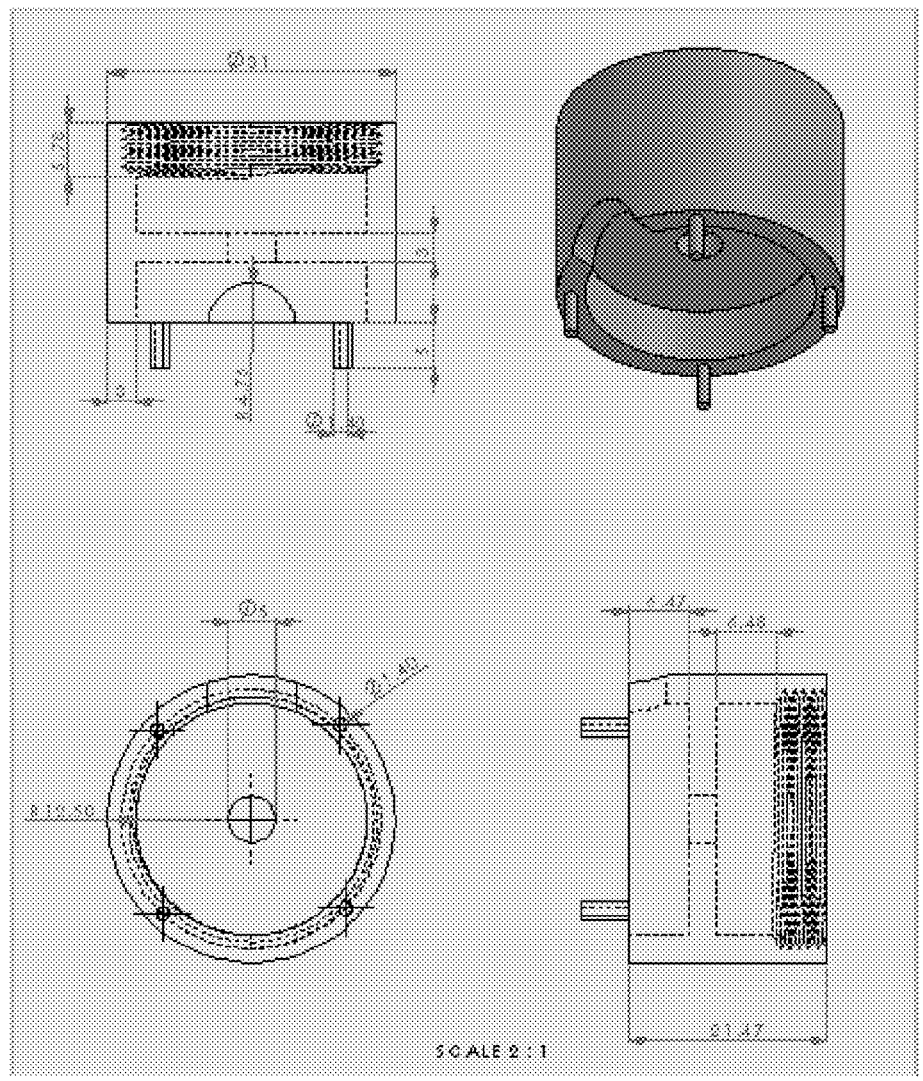
FIG. 9. Illustration of one embodiment of a handing mechanism.
Figure 10:
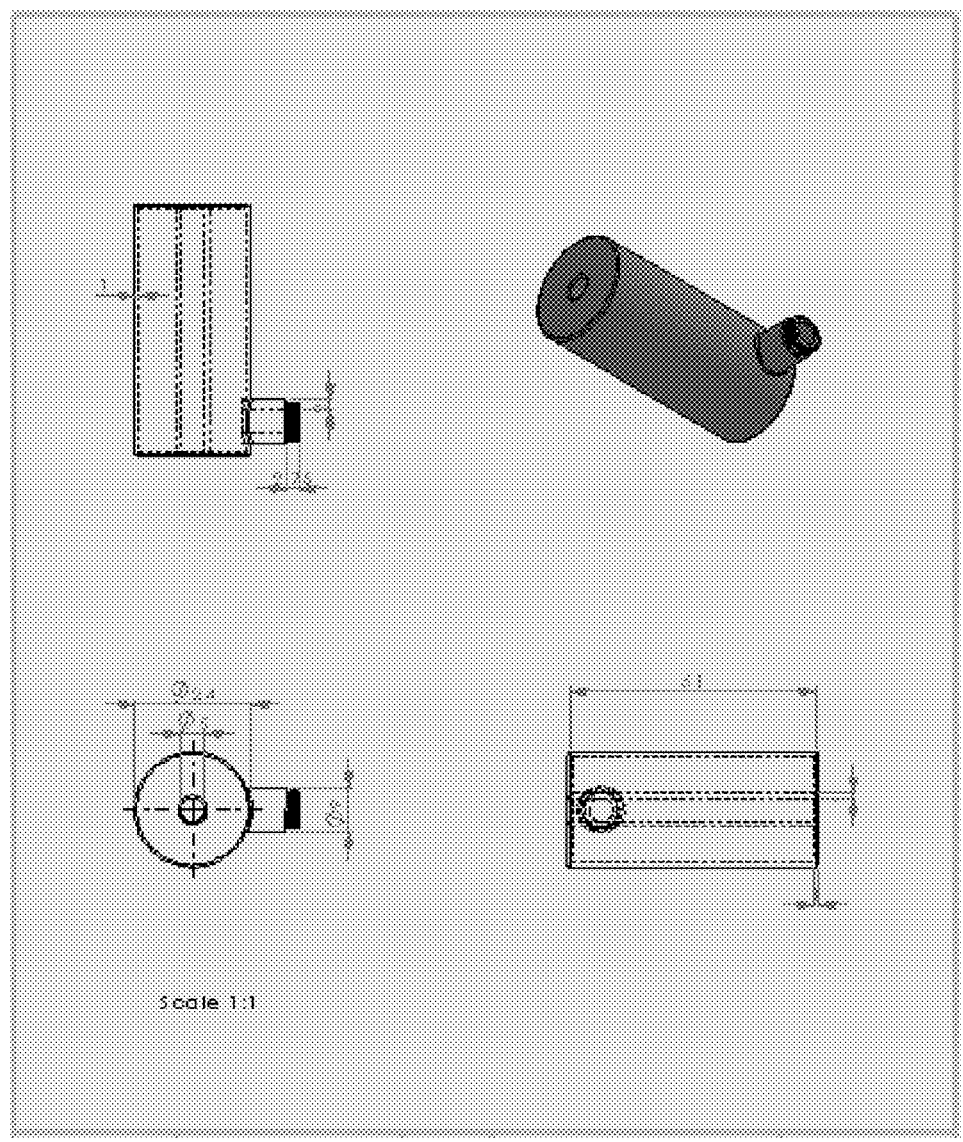
FIG. 10. Illustration of one embodiment of a reservoir.
Figure 11:
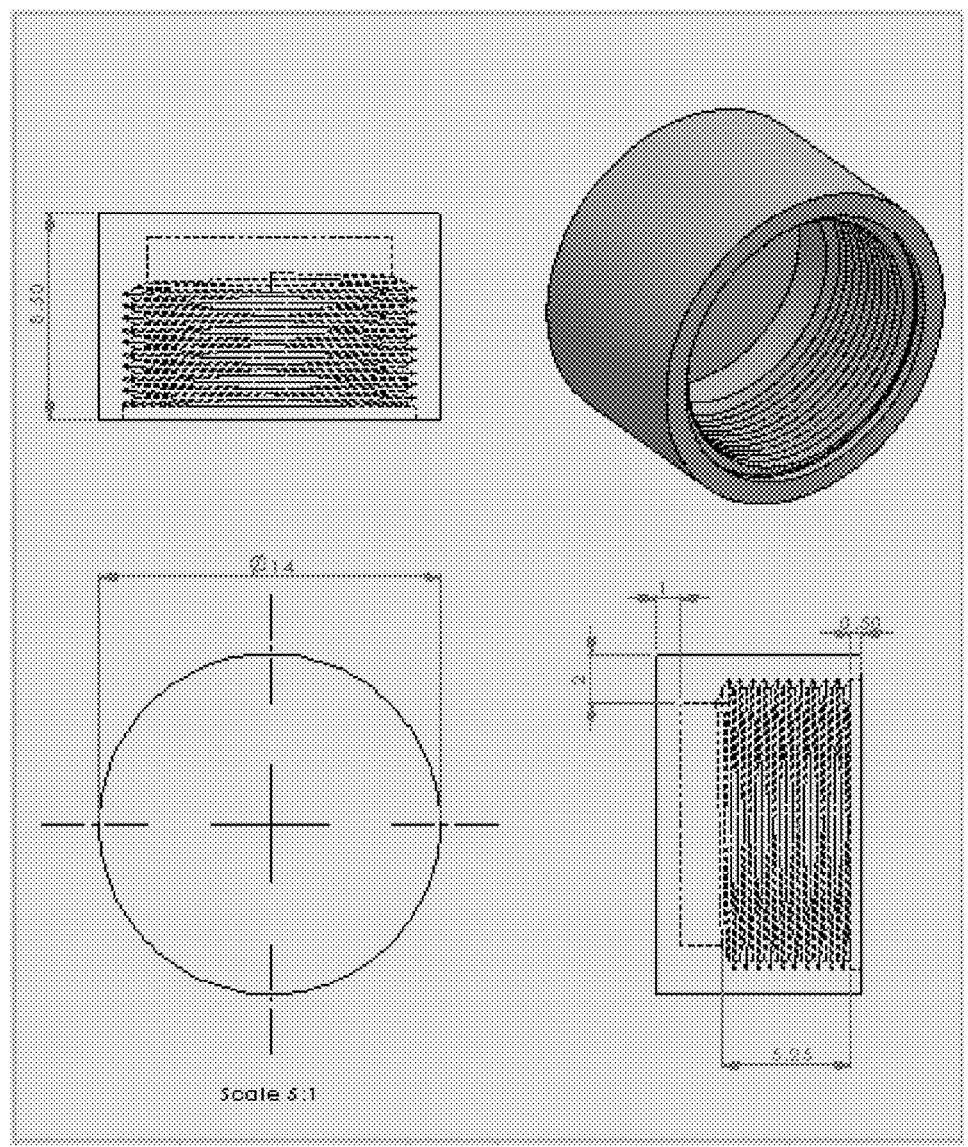
FIG. 11. Illustration of one embodiment of a reservoir cap.
Figure 12:
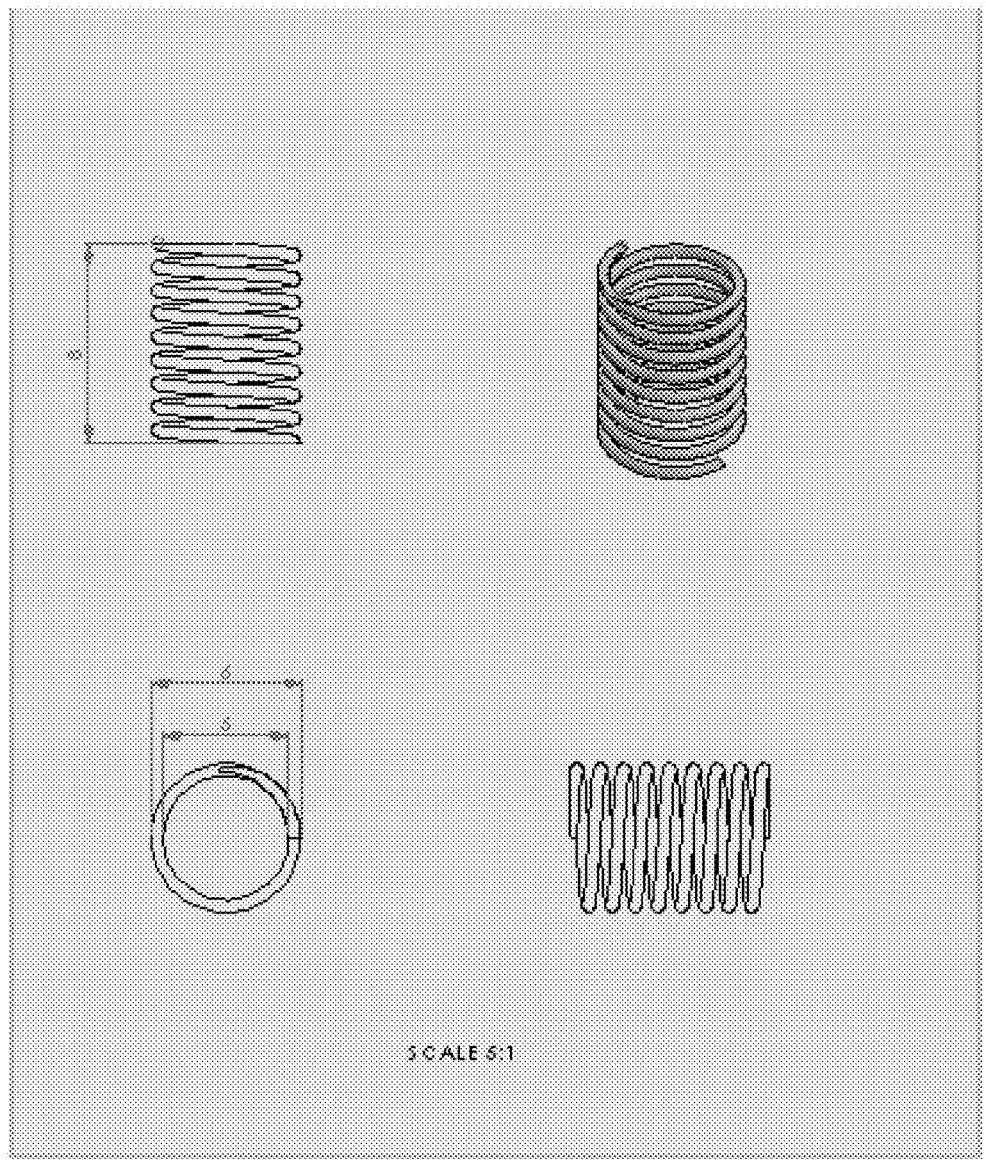
FIG. 12. Illustration of one embodiment of a spring component.
Figure 13:
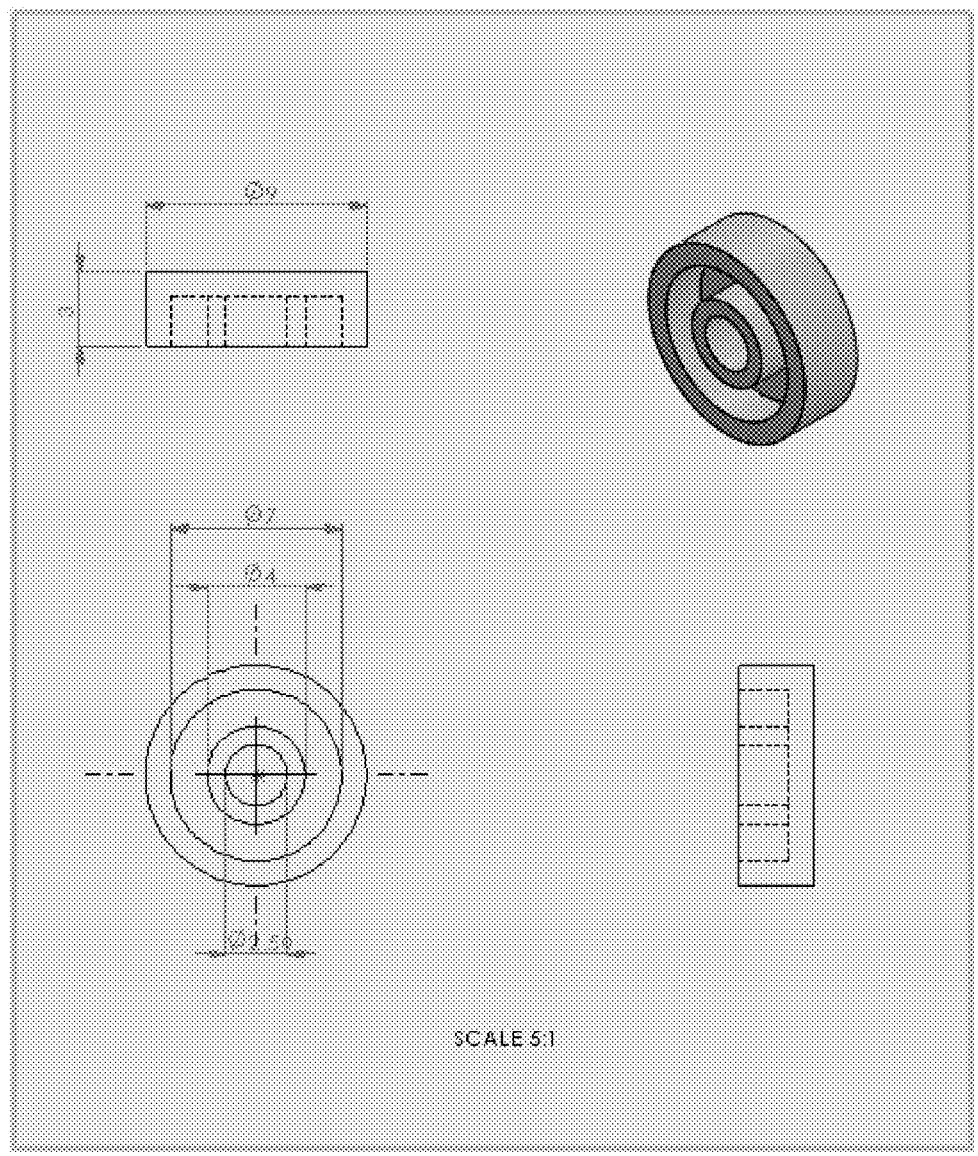
FIG. 13. Illustration of one embodiment of the terminal platform portion of the inner rod portion of the handing mechanism.
Figure 14:
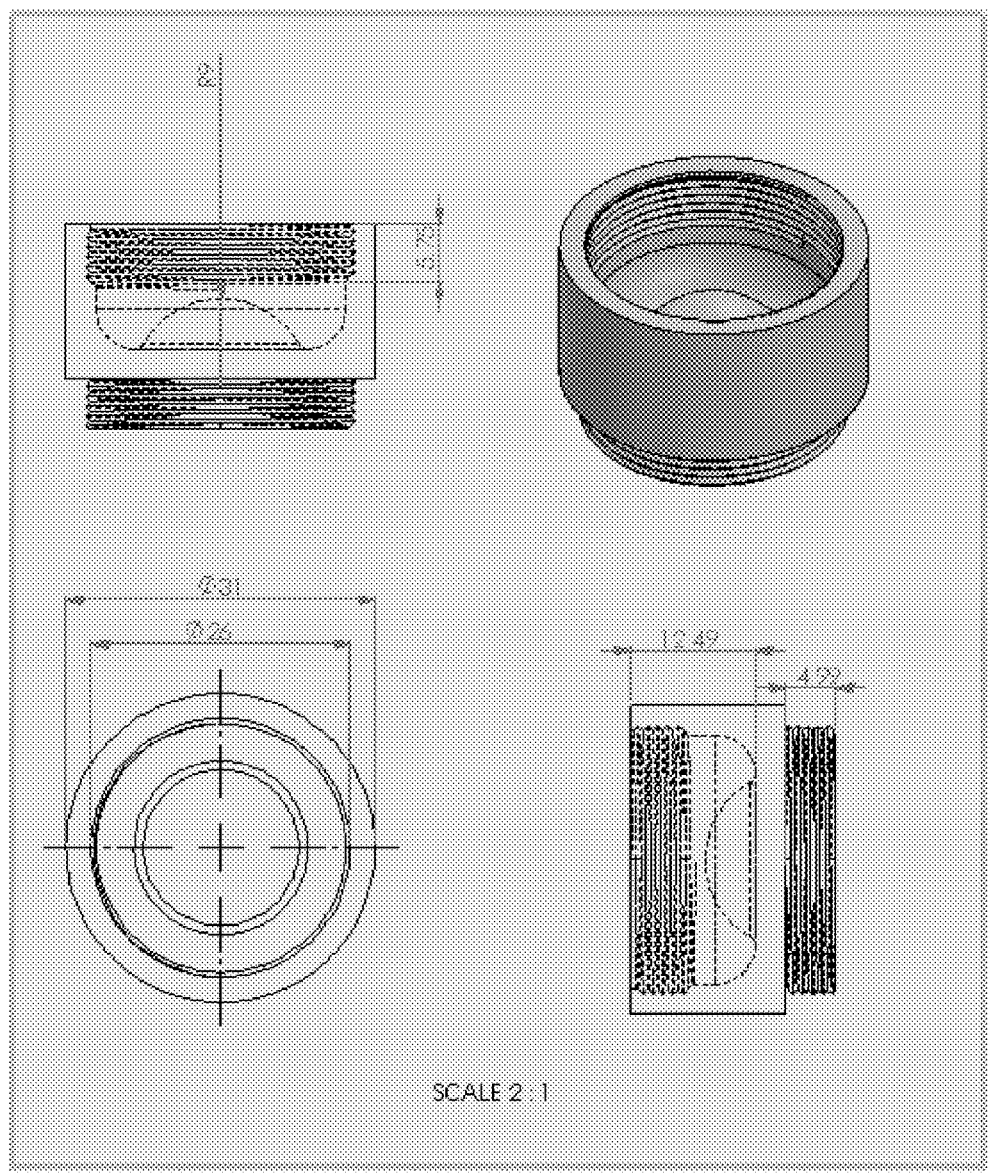
FIG. 14. Illustration of one embodiment of a lens storage segment 1.
Figure 15:
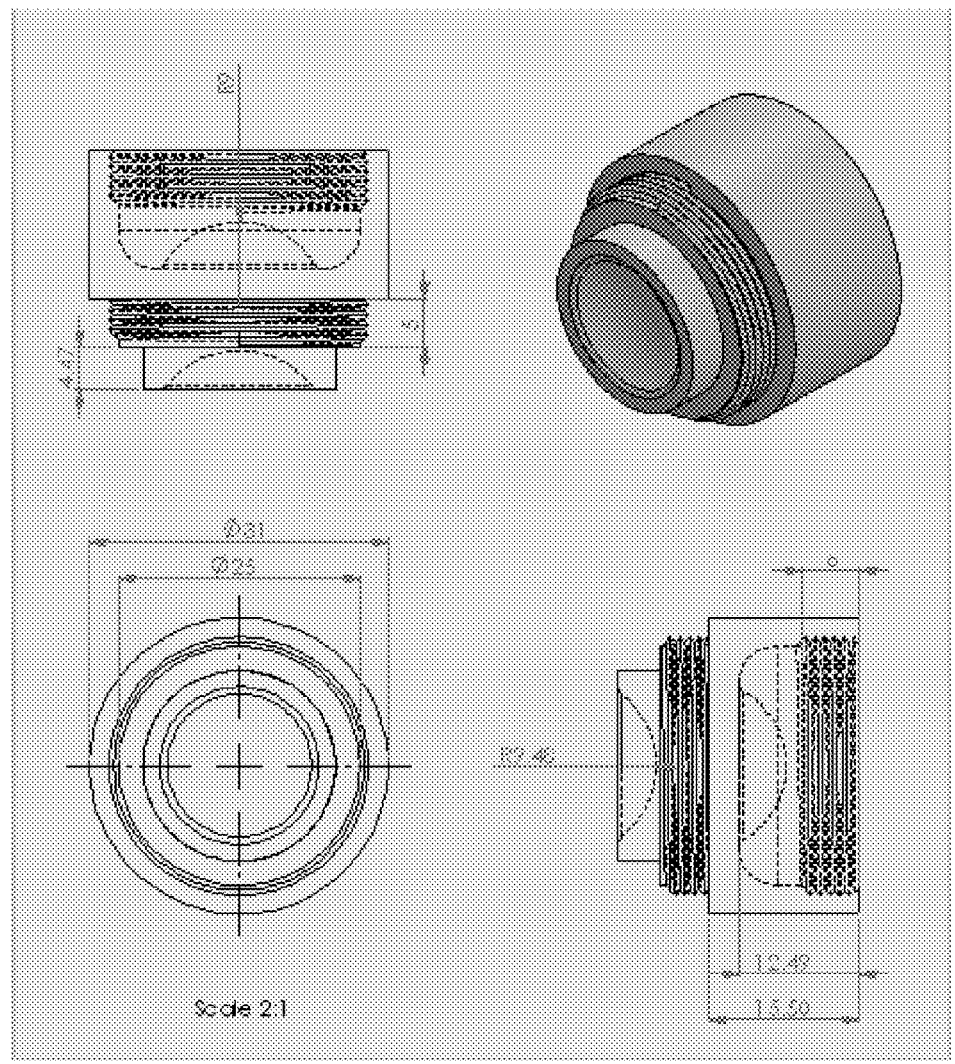
FIG. 15. Illustration of one embodiment of a lens storage segment 2.
Figure 16:
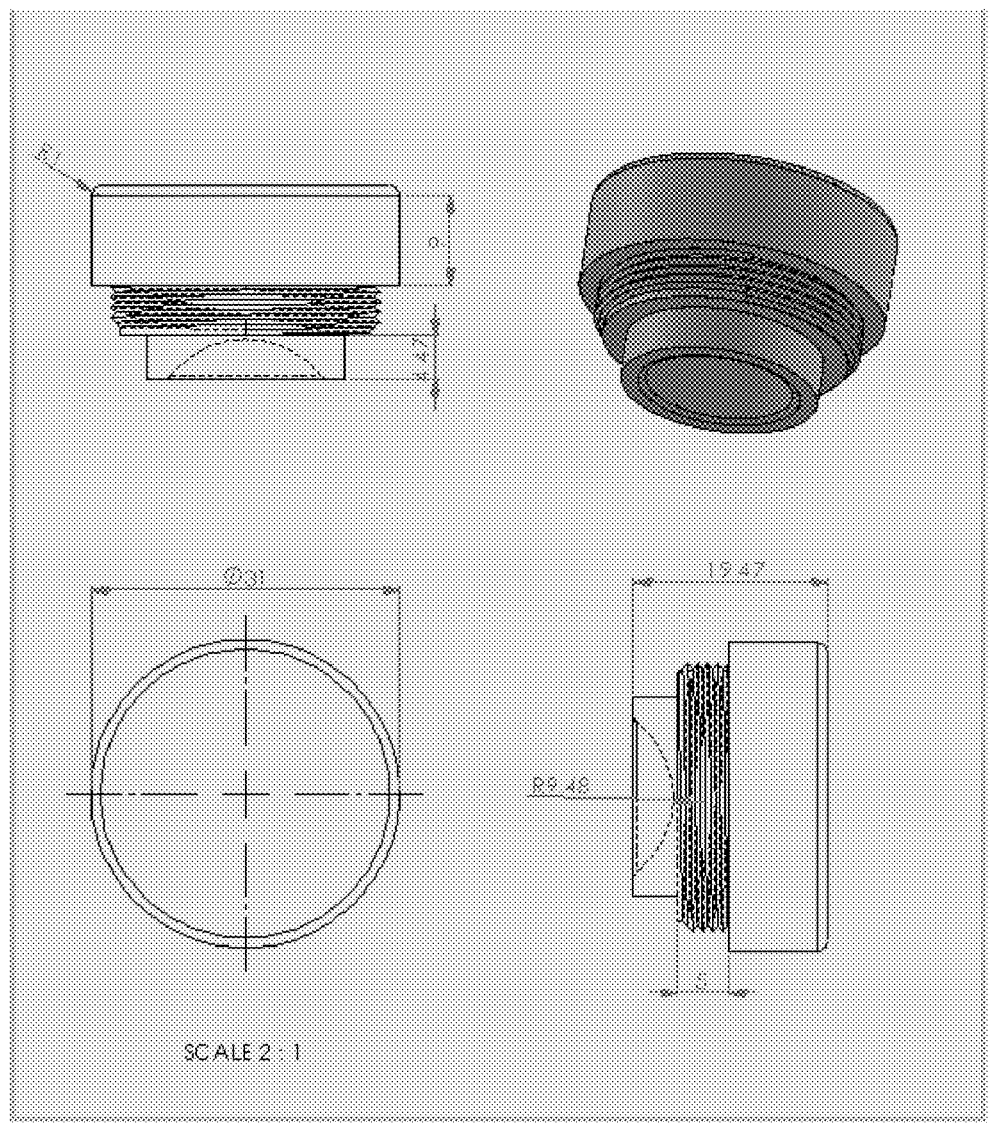
FIG. 16. Illustration of one embodiment of a lens storage segment cap.

FIG. 3 is an illustration of one embodiment of a second cap 120/220 having a threads 350 for connecting with an adjacent segment by a screw mechanism. FIG. 4 illustrates one embodiment of handling mechanism/fluid reservoir compartment 112/212 having a screw mechanisms 451 for connecting adjacent segments. Also shown in FIG. 4 is end wall 428 and opening 452 in the end wall 428 for receiving inner rod 234 and inner sheath 235. FIG. 5 illustrates one embodiment of lens-device interface 236. The lens-device interface can be covered with a flexible material to protect the eye during application and removal of a lens. FIG. 6 illustrates a soft flexible cover that is attached to the end of the lens-device interface and forms the contact surface for the lens and also provides movement for inner rod to act in attaching and removing a lens from the user's eye. FIG. 7 illustrates an embodiment of inner rod 234 having end 753 configured for attachment to button 237 and end 754 configured for attachment to lens-device interface 236. FIG. 8 illustrates one embodiment of inner rod 234 attached to lens-device interface 236. FIG. 9 illustrates an embodiment of disinfection segment 218. The illustration shows the disinfection segment having a lens storage segment positioning for disinfection. FIG. 10 illustrates one embodiment of the fluid reservoir having a valve or port for filling and emptying the reservoir. FIG. 11 illustrates an embodiment of first end cap 110/210. FIG. 12 illustrates one embodiment of spring 232 that is operatively coupled to inner rod 234. FIG. 13 illustrates an embodiment of button 237 that is connected to one end of inner rod 234. FIG. 14 illustrates an embodiment of a lens storage segment 214/216 having a lens support a screw mechanisms for connection to adjacent segments. FIG. 15 illustrates an embodiment of the complementary portion of segments adjacent to the lens storage segment and illustrate how the segments interact. FIG. 16 illustrates one embodiment of a segment designed to complement the lens support surface of the lens storage segment.

Figure 17:
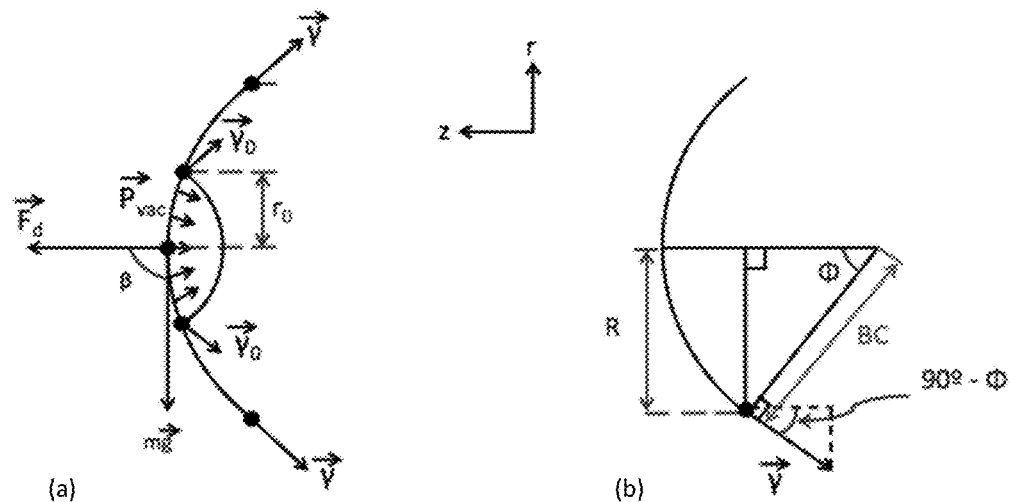
FIG. 17. General force balance diagram (a) and an additional diagram describing the angle at which surface tension acts on the lens with respect to the chosen coordinate system (b).

The general forces acting on the lens when worn determine the amount of force needed to remove the lens. To simplify the analysis, two dimensional diagrams and equations are assumed and used to solve for the sum of these general forces holding the lens to the eye. Another assumption to this analysis is that the shape of the lens is that of a perfect spherical cap. Therefore, only the components in the z-direction are of interest, since it is assumed that all radial components cancel each other out due to symmetry. Assuming a quasi-static situation, three cases of interest describe the process of removing the lens. In each of these three cases the goal was to solve for the force applied by a device to remove the contact lens from the eye. The first case (initial state) describes the force to start the process of removing the lens. The second case (intermediate state) takes into account the development of a vacuum between the lens and the wearer's eye, which acts against the device and creates an additional surface tension. The third case (final case) describes the moment at which the device is able to remove the lens from the eye. FIG. 17 shows this general force balance diagram and an additional diagram describing the angle at which surface tension acts on the lens with respect to the chosen coordinate system.

From FIG. 17, the force balances ($\Sigma \vec{F} = m\vec{a} = 0$; since quasi-static states are assumed) are set up and solved for the force required to remove the lens ($F_d$) in each of cases already described. Note that the coordinate system is always set in place so that the force performed by the device acts along the z-axis only. In other words, no matter what the position of the user is, the coordinate system is set so that the z-axis is always in the direction of the removal of the lens. Therefore, the angle β is the angle at which the weight of the contact lens acts with respect to the z-axis (it varies from $-\pi/2$ to $\pi/2$).

Case #1 ($r_0 = 0$):

$$F_{d,initial} = 2\pi R \gamma \cos\left(\frac{\pi}{2} - \phi\right) + mg\sin\beta \quad (1)$$

Case #2 ($0 < r_{0(t)} < R$):

$$F_{d,int.} = 2\pi R \gamma \cos\left(\frac{\pi}{2} - \phi\right) + 2\pi r_{0(t)} \gamma \cos\left(\frac{\pi}{2} - \phi\right) + P_{vac}\pi(r_{0(t)})^2 + mg\sin\beta \quad (2)$$

Case #3 ($r_{0(t)} = R$):

$$F_{d,final} = 4\pi R\gamma \cos\left(\frac{\pi}{2} - \phi\right) + (r_{0(t)})^2 + mg\sin\beta \quad (3)$$

The value of interest of $F_d$ is its maximum value, since this would be the minimal required force that has to be achieved by the device in order to remove the lens across all cases. This value was found using the following assumptions: R=7 mm (average radius of commercially available contact lenses);

$$\beta = \frac{\pi}{2}$$

(angle at which weight term is maximal and acts against the device; i.e. user is removing the lens upwards);

$$\phi = \sin^{-1}\left(\frac{R}{BC}\right)$$

(angle of curvature commercially available contact lenses, based on average radius and a range of base curvature values; 8 mm<BC<10 mm); γ=46 dyn/cm (surface tension between contact lenses and tear fluid or lubrication fluid); $P_{vac}$=1500 dyn/cm² (maximum pressure known to develop in the space between the lens and eye); m=0.0158 g (average mass of a soft contact lens).

Computing these equations, the highest value for $F_d$ was found to be 2.6787×10³ dyn (i.e. approximately 0.027 N). A copy of the MATLAB script used can be found in the appendix. This is the value for $F_d$ that is used for the remaining calculations in each of the solution concepts described in this document.

Surface pattern on concave surface at the handling tip. The minimum force required for removal of the contact lens from the user's eye was calculated in an earlier section. Using that value (2.6787×10³ dyn), the parameters for this device may be tuned in order to achieve a higher value of removal force, but within a reasonable safety factor. Recalling this device acts purely through surface tension forces for the removal process, the contact length L between the lens and the device is calculated as follows:

$$L = \frac{F_d}{\gamma} \quad \text{Equation 1}$$

where Fd is the minimal force required for removal, γ is the surface tension between contact lenses and tear fluid or lubrication fluid in (equal to 46 dyn/cm). Thus, the minimum contact length is calculated to be 58.23 cm. Through surface modification techniques it is possible to achieve this length in the form of a certain pattern. Therefore, an optimal contact length L will be determined through testing, and consequently a surface pattern that provides that contact length may be chosen.

It is also needed to calculate the stress exerted on the user's eye with such a force. For this purpose, equation 2 is used:

$$\sigma = \frac{F_d}{A} \quad \text{Equation 2}$$

where A is the projected cross-sectional area where the force is applied, and σ is the corresponding stress applied over the area A by the force Fd. Using a radius of 7 mm (as this is the average radius of a contact lens), and a value of 2.6787×10³ dyn (minimal force to remove lens from the eye with a device), the minimum stress σ min exerted on the user's eye was found to have a value of approximately 174 Pa. Therefore, it should be noted that the force applied with this device would in fact be far away from coming close to harming the user's eye. As discussed in the functional requirements and preliminary specifications section, the stress exerted in the users eye should be less than the tensile stress of the human cornea (3.41 MPa; this value corresponds to the maximum stress that can be exerted on the user's eye, σmax). Since the difference between σmin and σmax is of 4 orders of magnitude, there is a significant amount of room to increase the force applied by the device, without even approaching the maximum value of stress. In other words, the factor of safety in this device can be as large as 4 orders of magnitude.

Since the insertion mechanism consists of a push button that is pressed by the user to deposit the lens onto his or her eye, a spring constant (k) needs to be determined in order to choose the correct material and type of spring. From literature, the average force a human should apply during the motion of pushing a button ($F_{push}$) with a single finger is 7 N. Additionally, a displacement in the z-direction (Δz) of approximately 3 mm is assumed to be ideal for the comfort and safety of the user (this value may change when actual tests are conducted with this device). Therefore, a spring constant may be calculated using Hooke's law in order to using the correct material and size for the spring needed:

$$k = \frac{F_{push}}{\Delta z} \quad \text{Equation 3}$$

Therefore, the preliminary value for this spring constant is 2,333.3 N/m. ASTM standards on springs and their constants are readily available and will be used when assembling and testing this device so that the correct spring component is used. Similarly to the previous point discussed, equation 2 is used to estimate the stress exerted on the eye by this pushing force during the insertion process. However, the area of in this case should change since the piece of the device pushing the lens is now the inner sheath of the handling mechanism, which has a smaller radius than the concave tip of this handling part. Using a radius of 1 mm for this purpose, this stress is calculated to have a value of 45.5 kPa. Recalling that the tensile strength of the human cornea is 3.41 MPa, there is a difference of almost two orders of magnitude between the applied stress and the maximum value.

Figure 18:
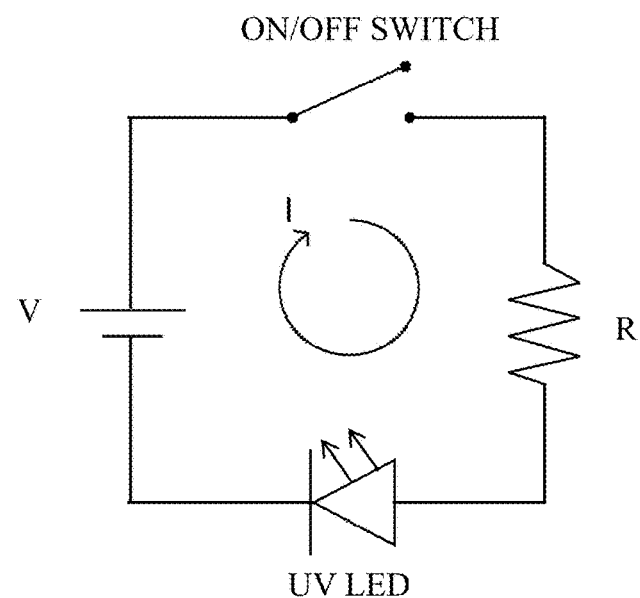
FIG. 18. Illustration of one embodiment of a UV LED circuit that may be used in the device.

The wavelength range of interest for killing bacteria spans from 200 to 300 nm with 254 nm corresponds to the optimal wavelength for eradicating these microorganisms. In one non-limiting embodiment, commercially available LEDs producing UV light around 250 nm can be used as a UV source. These commercially available UV LEDs require an operating current of 20 to 25 mA and a forward voltage of approximately 5 V. An example of a simple circuit with one UV LED with an added resistor and a power source is shown in FIG. 18. Note that the power source in this circuit shows only one battery cell, however the power source for the device might consist of several power cells arranged in series depending on their voltage. A resistor is added to the circuit so that current can be biased and limited in order for the correct amount of current to flow to the LED. It should also be noted that the device might need more than one UV LED or additional components, which will be determined once the project reaches the testing phase. Depending on the manufacturer's specifications for the UV LED, the resistance needed is calculated using Ohm's Law (Eq. 4), where R is resistance value (in Ω), V is voltage going through the LED (in V), I is operating current for the LED (in A). In other embodiments a UV lamp can be used as the UV source.

$$R = \frac{V}{I} \qquad \text{Equation 4}$$

The switch on this circuit serves the user in activating and deactivating the disinfection circuit. In certain aspects the circuit may be a circuit containing an automatic controller so that the user need not to manually control the time of disinfection. The switch can be conveniently located on the outside of the UV disinfection compartment so that the user may turn easily on the system.

The invention claimed is:

1. A contact lens storage and application device comprising:
   a body comprising a plurality of interlocking segments, the interlocking segments including (i) a disinfection segment, (ii) a handling mechanism/reservoir segment, (iii) a first lens storage container, and (iv) a second lens storage container, wherein each segment is removably connected to an adjacent segment or a cap;
   the disinfecting segment comprises a compartment housing a UV light source with the bottom portion configured to connect with a segment adjacent to the bottom portion and a top configured to connect with a segment adjacent to the top portion;
   the handling mechanism/reservoir segment comprises an outer wall forming a container having an open end configured to receive a cap and a closed end having an end wall configured to connect with an adjacent segment, within the container is a fluid reservoir having a fluid port extending to the exterior of the container to provide for movement of fluids in and out of the reservoir, a handling mechanism traverses the reservoir and is connected to the end wall and extends beyond the reservoir terminating in a lens delivery portion having a concave shape to complement and secure a lens, the handling portion has a central moveable rod that passes through the container end wall and is connected to a spring spacer and a button portion, the handling mechanism is configured such that pushing the button portion extends the central rod providing for the release of a lens during application and retraction of the rod provides for securing a lens during removal;
   the first lens storage segment comprises a first lens storage container having a convex lens support positioned in the bottom of the container with the base of the container configured to connect with a segment adjacent to the bottom portion and a top configured to connect with a segment adjacent to the top portion of the storage container; and
   the second lens storage segment comprises a second lens storage container having a convex lens support positioned in the bottom of the container with the base of the container configured to connect with a segment adjacent to the bottom portion and a top configured to connect with a segment adjacent to the top portion of the storage container.

2. The device of claim 1, wherein the UV light source is a light emitting diode (LED).

3. The device of claim 1, wherein the UV light source emits light at a wavelength of between 200 to 320 nm.

4. The device of claim 1, wherein the UV light source emits light of at least 254 nm.

5. The device of claim 1, wherein the surface of the lens delivery portion of the handling mechanism is patterned to reduce the amount of force needed to dissociate the delivery portion from a lens being delivered.

6. The device of claim 1, wherein the lens delivery portion of the handling mechanism has a protective material to protect the eye from scratching or puncture by the handling mechanism.

7. The device of claim 1, wherein the reservoir cross section is circular or polygonal.

8. The device of claim 1, wherein the device is at most 16 cm in length when fully assembled.

9. The device of claim 1, wherein the lens storage segments are at least 14.5 mm in diameter.

10. The device of claim 1, wherein the central rod has a diameter of about 2 mm.

11. The device of claim 1, wherein the diameter of the lens delivery portion has a diameter that is smaller than the diameter of a lens to be deployed.

12. The device of claim 1, further comprising one or more battery connected to the UV light source.

* * * * *